(12) United States Patent
Kim et al.

(10) Patent No.: US 11,471,425 B2
(45) Date of Patent: Oct. 18, 2022

(54) PHARMACEUTICAL COMPOSITION CONTAINING BROUSSOCHALCONE A AS ACTIVE INGREDIENT FOR TREATMENT OF INFLAMMATORY BOWEL DISEASE

(71) Applicant: BIOPHARMARESEARCHLAB CO., LTD., Anyang-si (KR)

(72) Inventors: Yoon Soo Kim, Seongnam-si (KR); Jin Woo Choi, Seoul (KR)

(73) Assignee: BIOPHARMARESEARCHLAB CO., LTD., Anyang-si (KR)

( * ) Notice: Subject to any disclaimer, the term of this patent is extended or adjusted under 35 U.S.C. 154(b) by 368 days.

(21) Appl. No.: 16/626,965

(22) PCT Filed: Jun. 29, 2018

(86) PCT No.: PCT/KR2018/007424
§ 371 (c)(1),
(2) Date: Dec. 27, 2019

(87) PCT Pub. No.: WO2019/004788
PCT Pub. Date: Jan. 3, 2019

(65) Prior Publication Data
US 2020/0138741 A1    May 7, 2020

(30) Foreign Application Priority Data

Jun. 30, 2017  (KR) .......................... 10-2017-0083320

(51) Int. Cl.
*A61K 31/12* (2006.01)
*A23L 33/10* (2016.01)
*A61P 1/04* (2006.01)

(52) U.S. Cl.
CPC .............. *A61K 31/12* (2013.01); *A23L 33/10* (2016.08); *A61P 1/04* (2018.01); *A23V 2002/00* (2013.01)

(58) Field of Classification Search
CPC ................................. A61K 31/12; A61P 1/04
See application file for complete search history.

(56) References Cited

FOREIGN PATENT DOCUMENTS

| CN | 103989746 B | 9/2016 |
|----|-------------|--------|
| CN | 105963284 A | 9/2016 |
| KR | 10-1674621 B1 | 11/2016 |

OTHER PUBLICATIONS

Zhi-Jiao Cheng et al., "Broussochalcone A, a potent antioxidant and effective suppressor of inducible nitric oxide synthase in lipopolysaccharide-activated macrophages", Biochemical Pharmacology, 2001, pp. 939-946, vol. 61.
Min-Hsiung Pan et al., "Anti-inflammatory activity of natural dietary flavonoids", Food Funct., 2010, pp. 15-31, vol. 1.
International Search Report of PCT/KR2018/007424 dated Jan. 2, 2019 [PCT/ISA/210].

*Primary Examiner* — Kevin E Weddington
(74) *Attorney, Agent, or Firm* — Sughrue Mion, PLLC

(57) ABSTRACT

The present invention relates to a pharmaceutical composition containing broussochalcone A as an active ingredient for prevention or treatment of inflammatory bowel disease. The pharmaceutical composition containing broussochalcone A as an active ingredient for prevention or treatment of inflammatory bowel disease of the present invention suppresses inflammation to ameliorate symptoms of weight loss, reduction in bowel length, diarrhea, and hemafecia, which result from inflammatory bowel disease, and has no side effects occurring in an existing drug medicine, and thus can be effectively used in the treatment of inflammatory bowel disease.

6 Claims, 5 Drawing Sheets

[Fig. 1]
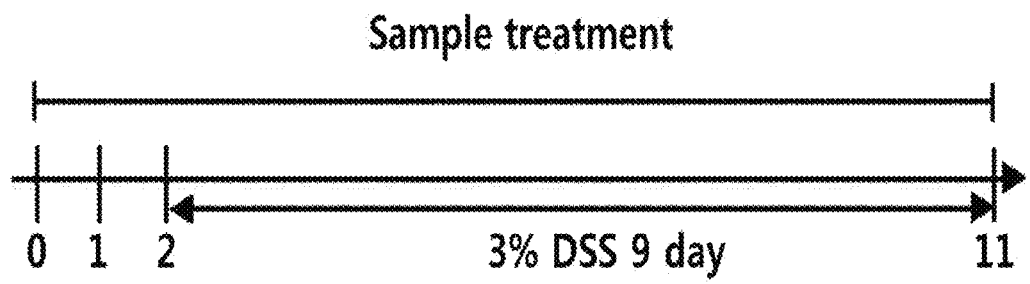
[Fig. 2]
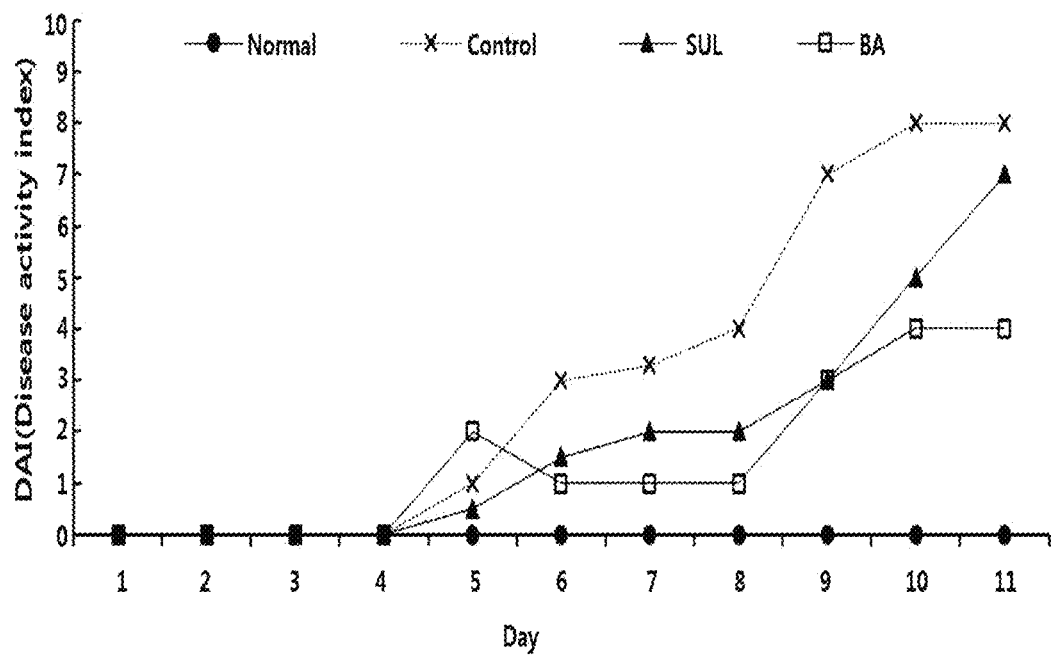

[Fig. 3]
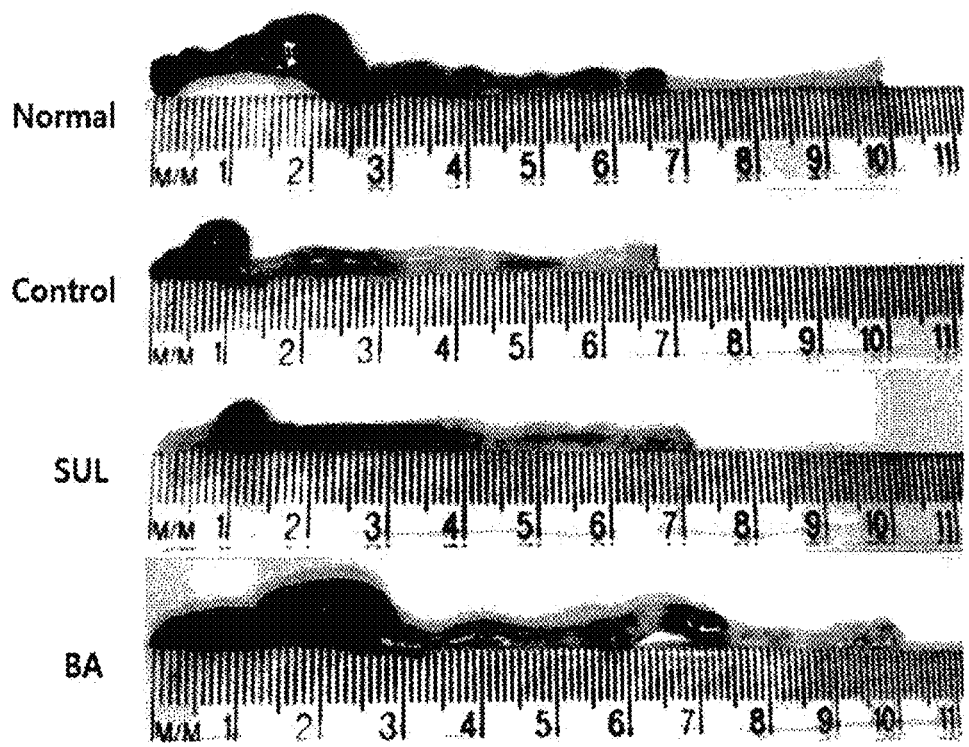
[Fig. 4]
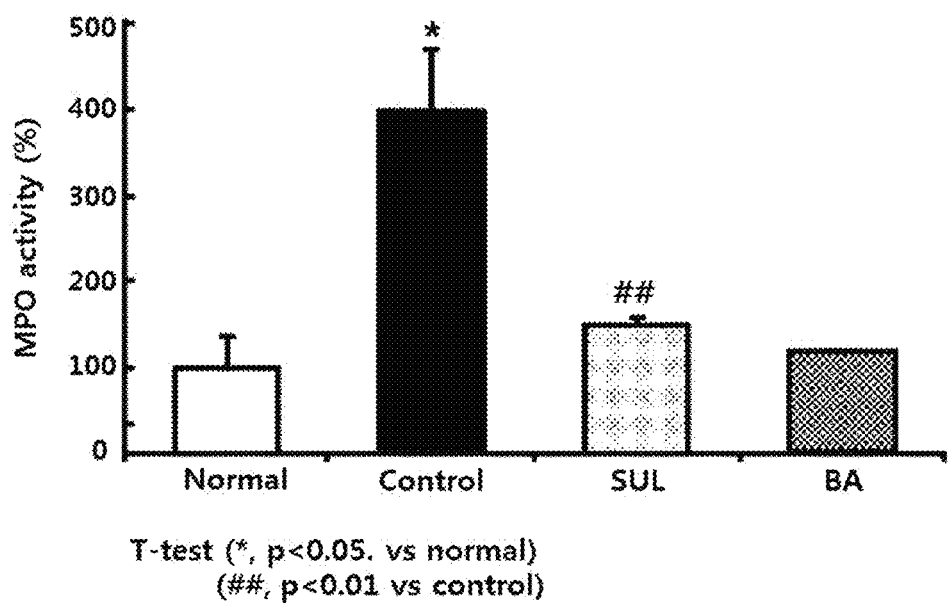

[Fig. 5]
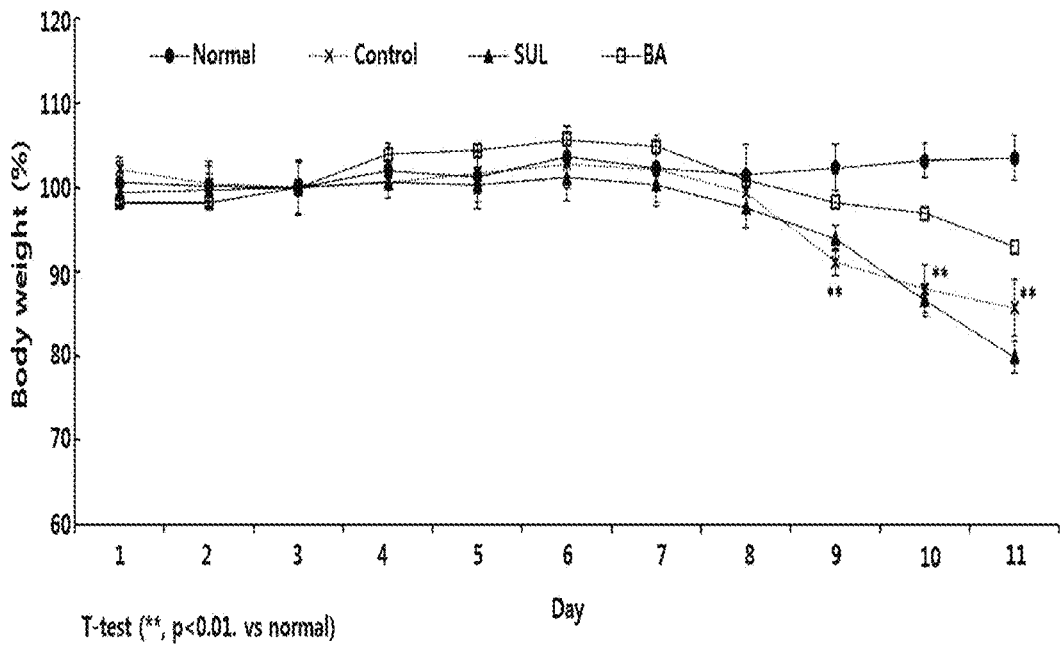
[Fig. 6]
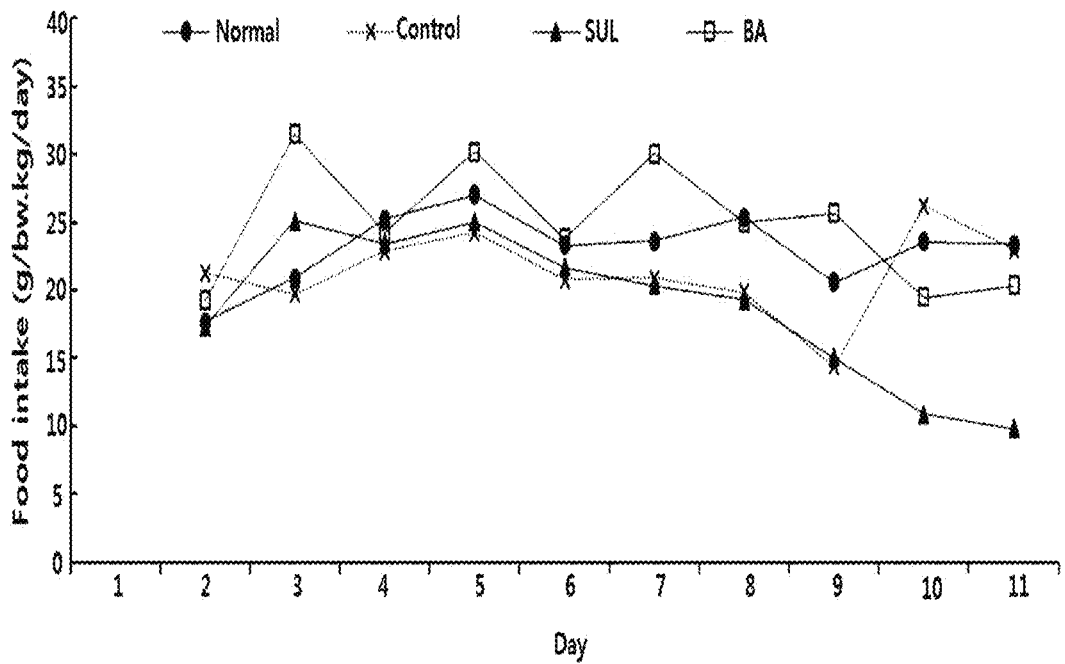

[Fig. 7]
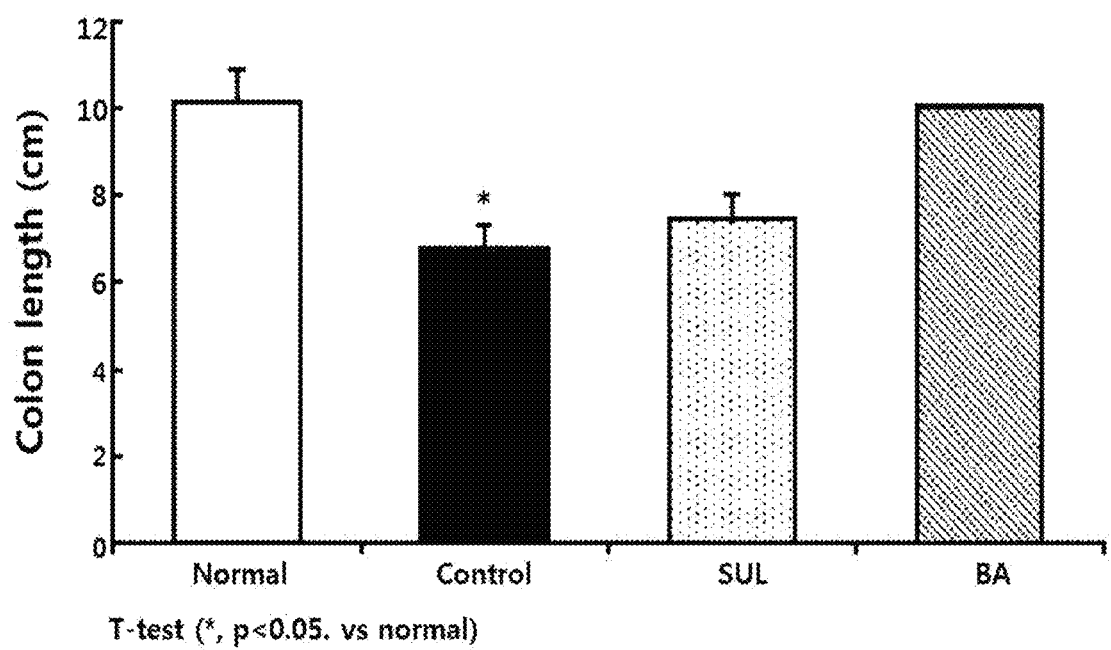

[Fig. 8]
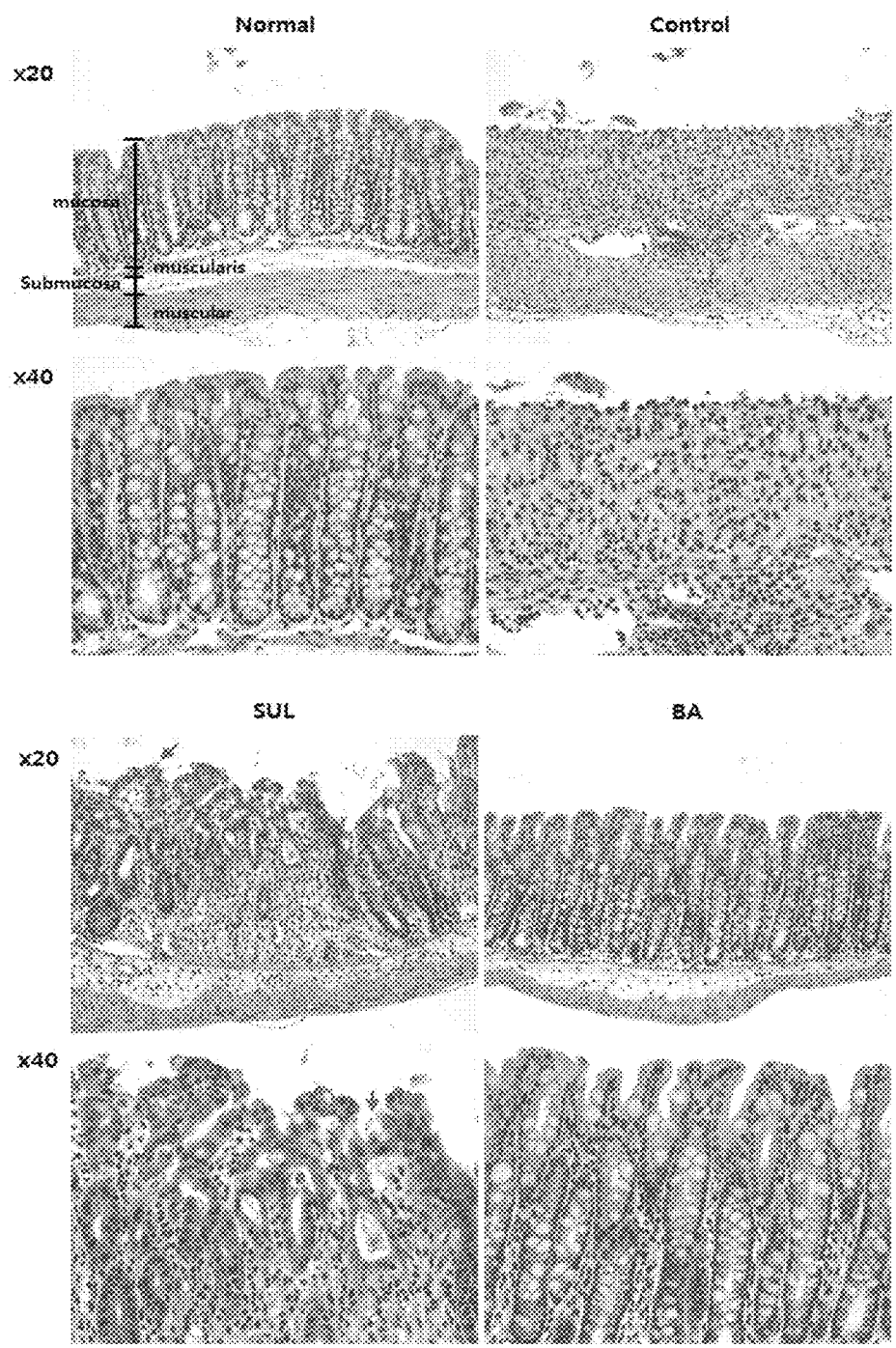

PHARMACEUTICAL COMPOSITION CONTAINING BROUSSOCHALCONE A AS ACTIVE INGREDIENT FOR TREATMENT OF INFLAMMATORY BOWEL DISEASE

CROSS REFERENCE TO RELATED APPLICATIONS

This application is a National Stage of International Application No. PCT/KR2018/007424, filed Jun. 29, 2018, claiming priority to Korean Patent Application No. 10-2017-0083320, filed Jun. 30, 2017.

TECHNICAL FIELD

The present invention relates to a pharmaceutical composition for preventing or treating inflammatory bowel disease, comprising broussochalcone A as an active ingredient.

BACKGROUND ART

Inflammatory bowel disease (IBD), which begins to develop in adolescence, causes chronic inflammation in the gastrointestinal tract and involves symptoms such as abdominal pain, fever, diarrhea, and melena. In general, inflammatory bowel disease is classified into ulcerative colitis and Crohn's disease. Ulcerative colitis is characterized by diffuse nonspecific inflammation of unknown cause mainly in the colon's mucosa, and involves symptoms such as decreased body weight, diarrhea, and hemafecia. Crohn's disease is characterized by granulomatous inflammation of unknown cause, by which ulcer, fibrosis, stenosis, and lesions are developed discontinuously in the entire digestive system from the mouth to the anus, and involves symptoms such as abdominal pain, chronic diarrhea, fever, and malnutrition.

Sulfasalazine is used as a therapeutic agent for inflammatory bowel disease. However, sulfasalazine has adverse effects such as nausea, vomiting, loss of appetite, headache, and anemia. Therefore, there is a need for continuous research and development on a therapeutic agent for inflammatory bowel disease which is safe and has no adverse effects.

DISCLOSURE OF INVENTION

Technical Problem

As a result of studies to develop a therapeutic agent for inflammatory bowel disease, the present inventors have identified that broussochalcone A suppresses inflammation in ulcerative colitis-induced mice without causing adverse effects, thereby completing the present invention.

Solution to Problem

In an aspect of the present invention, there is provided a pharmaceutical composition for preventing or treating inflammatory bowel disease, comprising broussochalcone A as an active ingredient.

In another aspect of the present invention, there is provided a health functional food for ameliorating inflammatory bowel disease, comprising broussochalcone A as an active ingredient.

In yet another aspect of the present invention, there is provided a use of broussochalcone A for treatment of inflammatory bowel disease.

In still yet another aspect of the present invention, there is provided a use of broussochalcone A for manufacture of a medicament for treating inflammatory bowel disease.

In still yet another aspect of the present invention, there is provided a method for treating inflammatory bowel disease, comprising a step of administering broussochalcone A to a subject in need thereof.

Advantageous Effects of Invention

The pharmaceutical composition for preventing or treating inflammatory bowel disease, which comprises broussochalcone A as an active ingredient, of the present invention suppresses inflammation so that symptoms, such as decreased body weight, decreased colon length, diarrhea, and hemafecia, occurring in inflammatory bowel disease are alleviated, and has no adverse effects observed in existing therapeutic drugs. Thus, the pharmaceutical composition can be usefully used for treatment of inflammatory bowel disease.

BRIEF DESCRIPTION OF DRAWINGS

FIG. 1 illustrates a schematic diagram for an animal experiment plan using ulcerative colitis-induced mice.

FIG. 2 illustrates a graph showing disease activity index of ulcerative colitis-induced mice, which have received saline, sulfasalazine, or broussochalcone A, in terms of scores.

FIG. 3 illustrates photographs for the colon length of ulcerative colitis-induced mice which have received saline, sulfasalazine, or broussochalcone A.

FIG. 4 illustrates a graph showing MPO activity in colon tissues of ulcerative colitis-induced mice which have received saline, sulfasalazine, or broussochalcone A.

FIG. 5 illustrates a graph showing changes in body weight of ulcerative colitis-induced mice which have received saline, sulfasalazine, or broussochalcone A.

FIG. 6 illustrates a graph showing food intake by ulcerative colitis-induced mice which have received saline, sulfasalazine, or broussochalcone A.

FIG. 7 illustrates a graph showing the colon length of ulcerative colitis-induced mice which have received saline, sulfasalazine, or broussochalcone A.

FIG. 8 illustrates photographs obtained by subjecting, to hematoxylin and eosin (H&E) staining, colon tissues of ulcerative colitis-induced mice which have received saline, sulfasalazine, or broussochalcone A.

BEST MODE FOR CARRYING OUT THE INVENTION

Hereinafter, the present invention will be described in detail.

In an aspect of the present invention, there is provided a pharmaceutical composition for preventing or treating inflammatory bowel disease, comprising broussochalcone A as an active ingredient.

The broussochalcone A may be a compound represented by Formula 1.

[Formula 1]

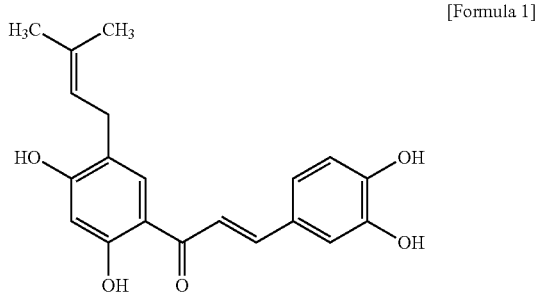 [SMILES: CC(C)=CCc1cc(C(=O)/C=C/c2ccc(O)c(O)c2)c(O)cc1O]

The inflammatory bowel disease may be any one disease selected from the group consisting of Crohn's disease, ulcerative colitis, intestinal Bechet's disease, and enteritis.

The present inventors made an animal experiment plan using ulcerative colitis-induced mice to identify a therapeutic effect of broussochalcone A on inflammatory bowel disease (FIG. 1).

Specifically, the ulcerative colitis-induced mice were allowed to receive broussochalcone A specimen (hereinafter referred to as "BA specimen"), and then disease activity index (DAI) of the ulcerative colitis-induced mice was measured by converting their fecal consistency and color into scores. As a result, a control group and a positive control group exhibited high DAI, whereas an experimental group having received the BA specimen exhibited lower DAI than the control group and the positive control group (FIG. 2).

In addition, in the ulcerative colitis-induced mice, the colon was extracted and measured for changes in length. As a result, the experimental group having received the BA specimen did not exhibit decreased colon length which was observed in the control group and the positive control group having received an anti-inflammatory agent; and the experimental group was measured to have a similar colon length to a normal group (FIGS. 3 and 4).

In addition, changes in body weight and food intake were observed by measuring the body weight and food intake at daily intervals from the start (day 0) to the end (day 11) of the animal experiment. As a result, the control group and the positive control group exhibited a great decrease in body weight, whereas the experimental group having received the BA specimen exhibited less decrease in body weight than the control group and the positive control group (FIG. 5). In addition, the experimental group having received the BA specimen generally exhibited an increase in food intake as compared with the normal group. On the other hand, due to adverse effects caused by the anti-inflammatory agent, the positive control group exhibited a decrease in food intake (FIG. 6).

In addition, a degree of inflammatory response was measured by measuring activity of myeloperoxidase (MPO), an inflammatory indicator, in tissues of the extracted colon. As a result, the control group exhibited about 4-fold higher MPO activity than the normal group, and the experimental group having received the BA specimen was measured to have similar MPO activity to the normal group (FIG. 7).

Furthermore, tissues of the extracted colon were subjected to hematoxylin and eosin (H&E) staining, and then histological analysis was performed. As a result, for the control group and the positive control group, it was identified that colon tissues thereof have lost goblet cells and surface epithelium, and it was identified that many immune cells also have penetrated the colon tissues. On the other hand, for the experimental group having received the BA specimen, it was observed that colon tissues thereof have a similar structure to the normal group (FIG. 8).

From these results, it was identified that the pharmaceutical composition for preventing or treating inflammatory bowel disease, which comprises broussochalcone A as an active ingredient, has an excellent inflammation inhibitory effect as compared with sulfasalazine conventionally used for treatment of inflammatory bowel disease, and has no adverse effects. Therefore, the pharmaceutical composition of the present invention can be usefully used for prevention or treatment of inflammatory bowel disease.

The pharmaceutical composition may further comprise suitable carriers, excipients, and diluents commonly used in manufacture of pharmaceutical compositions. In addition, the pharmaceutical composition may be formulated in the form of oral preparations such as powders, granules, tablets, capsules, suspensions, emulsions, syrups, and aerosols, external preparations, suppositories, or sterile injection solutions according to conventional methods, and used. Suitable formulations known in the art may be those disclosed in Remington's Pharmaceutical Science (Mack Publishing Company, Easton Pa.).

In addition, in the pharmaceutical composition, examples of the carrier, the excipient, and the diluent may include lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinyl pyrrolidone, water, methyhydroxybenzoate, propylhydroxybenzoate, talc, magnesium stearate, and mineral oil. In a case where the composition is formulated, preparation thereof may be made using diluents or excipients such as fillers, extenders, binders, wetting agents, disintegrants, and surfactants which are commonly used.

Solid preparations for oral administration may include tablets, pills, powders, granules, capsules, and the like. Such solid preparations may be prepared by mixing the composition with at least one excipient, for example, starch, calcium carbonate, sucrose, lactose, and gelatin. In addition to simple excipients, lubricants such as magnesium stearate and talc may also be used. Liquid preparations for oral administration include suspensions, solutions, emulsions, syrups, and the like. The liquid preparations may contain various excipients such as wetting agents, sweeteners, fragrances, and preservatives, in addition to water and liquid paraffin which are commonly used simple diluents.

Preparations for parenteral administration may include sterile aqueous solutions, non-aqueous solvents, suspensions, emulsions, lyophilized preparations, and suppositories. For the non-aqueous solvents and the suspensions, propylene glycol, polyethylene glycol, vegetable oil such as olive oil, injectable ester such as ethyl oleate, and the like may be used. As bases of the suppositories, Witepsol, macrogol, Tween 61, cacao fat, laurin fat, glycerogelatin, and the like may be used.

A preferred dose of the pharmaceutical composition varies depending on the patient's condition and body weight, severity of disease, drug form, route of administration, and duration, and may be suitably chosen by those skilled in the art. For a desired effect, a daily dose of the pharmaceutical composition may be administered in an amount of 1 mg/kg to 10,000 mg/kg, and may be administered once a day or several times a day.

The pharmaceutical composition may be administered to an individual via various routes. All modes of administration are expectable, for example, administrations may be made by oral, rectal or intravenous, intramuscular, subcutaneous, intrauterine, or intracerebroventricular injection. In an embodiment of the present invention, the pharmaceutical composition was orally administered.

The pharmaceutical composition may be used alone or in combination with methods in which surgery, hormone therapy, chemotherapy, and biological response modifiers are used, for prevention and treatment of inflammatory bowel disease.

In another aspect of the present invention, there is provided a health functional food for ameliorating inflammatory bowel disease, comprising broussochalcone A as an active ingredient.

The health functional food may be prepared in various forms, such as tablets, capsules, powders, granules, liquids, and pills, in order to obtain effects that are useful for amelioration of inflammatory bowel disease.

The health functional food according to the present invention may further comprise additives which can be commonly used in food compositions to improve odor, taste, appearance, and the like. For example, the additive may include vitamins A, C, D, E, B1, B2, B6, B12, niacin, biotin, folate, pantothenic acid, and the like. In addition, the additive may include minerals such as zinc (Zn), iron (Fe), calcium (Ca), chromium (Cr), magnesium (Mg), manganese (Mn), and copper (Cu). In addition, the additive may include amino acids such as lysine, tryptophan, cysteine, and valine.

In addition, to the health functional food may be added food supplements such as preservatives (potassium sorbate, sodium benzoate, salicylic acid, sodium dehydroacetate, and the like), disinfectants (bleaching powder and high bleaching powder, sodium hypochlorite, and the like), antioxidants (butylhydroxyanisol (BHA), butylhydroxytoluene (BHT), and the like), coloring agents (tar pigments and the like), color-developing agents (sodium nitrite and the like), bleaching agents (sodium sulfite), seasonings (monosodium glutamate (MSG) and the like), sweeteners (dulcin, cyclamate, saccharin sodium, and the like), flavors (vanilin, lactones, and the like), swelling agents (alum, potassium hydrogen D-tartrate, and the like), fortifiers, emulsifiers, thickeners (gelling agents), film-forming agents, gum base agents, antifoaming agents, solvents, and improving agents. The supplements may be selected depending on the type of food and used in appropriate amounts.

In yet another aspect of the present invention, there is provided a use of broussochalcone A for treatment of inflammatory bowel disease.

In still yet another aspect of the present invention, there is provided a use of broussochalcone A for manufacture of a medicament for treating inflammatory bowel disease.

In still yet another aspect of the present invention, there is provided a method for treating inflammatory bowel disease, comprising a step of administering broussochalcone A to a subject in need thereof. Here, the subject may be a mammal, preferably a human. The pharmaceutical composition is as described above.

Regarding route of administration, dose, and frequency of administration, the pharmaceutical composition may be administered to a subject in various ways and amounts depending on the patient's condition and the presence or absence of adverse effects. Mode of administration, dose, and frequency of administration which are optimal may be selected in appropriate ranges by those skilled in the art. In addition, the pharmaceutical composition may be administered in combination with other drugs or physiologically active substances whose therapeutic effects are known for the disease to be treated, or may be formulated in the form of a combination preparation with other drugs.

MODE FOR THE INVENTION

Hereinafter, the present invention will be described in detail by way of examples. However, the following examples are given only for illustrating the present invention, and the present invention is not limited to the following examples.

Example 1. Ulcerative Colitis Induction in Mice and Drug Administration

7-Week-old C57BL/6J mice were purchased from Central Lab. Animal Inc. (Seoul, Korea) and acclimatized for 7 days to an experimental environment, which was maintained at constant humidity and constant temperature under a 12-hour light/dark cycle, while allowing them to access solid feed and water ad libitum. After 7 days of acclimatization period, the mice were divided into normal group, control group, positive control group (sulfasalazine), and BA experimental group (broussochalcone A) (Table 1).

TABLE 1

| Group | Drinking water | Number of individuals (n) |
|---|---|---|
| Normal group | Water | 4 |
| Control group | Water supplemented with 3% (w/v) DSS | 4 |
| Positive control group (sulfasalazine) | | 4 |
| BA experimental group (broussochalcone A) | | 1 |

The normal group received a mixture of 9 ml of Koliphor EL (Sigma, USA) and 1 ml of DMSO at the same dose as the BA experimental group. The normal group was allowed to access water ad libitum during the experimental period.

The control group received a mixture of 9 ml of Koliphor EL (Sigma, USA) and 1 ml of DMSO at the same dose as the BA experimental group. Starting from day 3, the control group was allowed to access ad libitum to a mixture obtained by mixing drinking water with 3% (w/v) dextran sodium sulfate (DSS) (MP Biomedicals, USA).

Sulfasalazine (Sigma, USA) was quantified at 150 mg and dissolved in 1 ml of DMSO to prepare an SUL solution. 9 ml of Koliphor EL was diluted in PBS to prepare a 10% (v/v) Koliphor solution. The SUL solution was mixed with 9 ml of 10% (v/v) Koliphor solution to prepare an SUL specimen. Then, the SUL specimen was quantified and orally administered at 100 μl/10 g·body weight (bw) to the positive control group. Starting from day 3, the positive control group was allowed to access ad libitum to a mixture obtained by mixing drinking water with 3% (w/v) dextran sodium sulfate.

Broussochalcone A (Natural Products Bank, Korea) was quantified at 20 mg and dissolved in 1 ml of DMSO to prepare a BA solution. 9 ml of Koliphor EL was diluted in PBS to prepare a 10% (v/v) Koliphor solution. The BA solution was mixed with 9 ml of 10% (v/v) Koliphor solution to prepare a BA specimen. Then, the BA specimen was quantified and orally administered at 100 μl/10 g·body weight (bw) to the BA experimental group. Starting from day 3, the BA experimental group was allowed to access ad libitum to a mixture obtained by mixing drinking water with 3% (w/v) dextran sodium sulfate (FIG. 1).

Example 2. Identification of Changes in Disease Activity Index (DAI) Following Intake of Broussochalcone a During the experimental period, the mice were caused to defecate once a day. Feces appearance was observed and fecal occult blood was observed using the Beckman Coulter Hemoccult Single Slides (Beckman Coulter, Inc., USA). The observation results were expressed in scores according to the criteria in Table 2.

TABLE 2

| Score | Fecal consistency | Fecal color |
|---|---|---|
| 0 | Moderate | Moderate |
| 1 | Slight soft | Brown |
| 2 | Soft | Orange |
| 3 | Very soft | Scarlet |
| 4 | Loose | Red |

Disease activity index (DAI)=(Fecal consistency+ fecal color)/2

Table 2 shows a table in which scores for measuring DAI are indicated.

As a result of measuring DAI of the mice for which ulcerative colitis had been induced by DSS, it was identified that the control group and the positive control group exhibited high DAI, whereas the BA experimental group exhibited lower DAI than the control group (FIG. 2).

Example 3. Identification of Changes in Colon Length Following Intake of Broussochalcone A On day 11, the mice were sacrificed by intraperitoneal injection of Alfaxan (Jurox Pty Limited, Australia), and then the colon, which ranges from the cecum site to the site immediately before the anus, was extracted. After all colonic contents in the colon tissues were removed, some specimens were fixed in 4% (v/v) paraformaldehyde fixative for use as pathological specimens, and the other specimens were stored frozen at −80° C. for molecular biological analysis.

As a result of checking the colon length of the mice for which ulcerative colitis had been induced by DSS, it was identified that the control group had a colon length which was about 3.2 cm shorter than that of the normal group. In addition, it was identified that the positive control group had a colon length which was about 2.8 cm shorter than that of the normal group. On the other hand, the BA experimental group was measured to have a colon length similar to that of the normal group, and did not exhibit decreased colon length observed in the control group and the positive control group (FIGS. 3 and 4).

Example 4. Identification of Changes in Body Weight and Food Intake Following Intake of Broussochalcone A Since ulcerative colitis-induced animals lose weight, a symptom-alleviating effect was checked by measuring changes in body weight.

For the respective normal group, control group, positive control group, and BA experimental group prepared in Example 1, the body weight was measured using a precision balance at the start of the experiment (day 0), and changes in body weight were measured at daily intervals for comparison.

As a result of measuring the body weight of the ulcerative colitis-induced mice, the normal group exhibited an about 5% increase in body weight, and the control group exhibited an about 15% decrease in body weight. In addition, it was identified that the positive control group exhibited an about 20% decrease in body weight, and the BA experimental group exhibited an about 5% decrease in body weight (FIG. 5).

In addition, as a result of measuring the food intake by the ulcerative colitis-induced mice, the normal group and the control group exhibited similar food intake, and the BA experimental group generally exhibited an increase in food intake as compared with the normal group. On the other hand, the positive control group exhibited a decrease in food intake. Such a decrease in food intake is thought to be due to adverse effects of the drug (FIG. 6).

Example 5. Identification of Changes in Myeloperoxidase (MPO) Activity Following Intake of Broussochalcone A For the mice for which ulcerative colitis had been induced by DSS, activity of MPO, an inflammatory indicator, was checked.

The colon tissues stored frozen in Example 3 were analyzed using the WO Colorimetric Activity Assay Kit (Sigma, USA), in which absorbance at a wavelength of 412 nm was measured three times to calculate an average value.

As a result, it was identified that the control group exhibited an about 4-fold increase in MPO activity as compared with the normal group. On the other hand, the positive control group exhibited an about 1.5-fold increase in MPO activity as compared with the normal group, and the BA experimental group did not exhibit significantly different MPO activity as compared with the normal group (FIG. 7).

Example 6. Identification of Histological Changes in Colon Tissue Following Intake of Broussochalcone A The colon tissues stored frozen in Example 3 were fixed in 4% paraformaldehyde for 48 hours and then washed with PBS. The fixed tissues were embedded in paraffin, cut into 4 µm thickness, and stained with hematoxylin and eosin. Then, the stained tissues were observed under a microscope.

As a result, for the control group, a decrease in number of goblet cells and damages to surface epithelium and the entire tissue were identified in the colon tissues, and it was found that many immune cells had penetrated the colon tissues. For the positive control group, it was identified that the structure of the mucosa was partially maintained in the colon tissues; however, it was identified that the colon tissues had lost goblet cells and surface epithelium. In addition, for the positive control, it was identified that many immune cells had penetrated the colon tissues. On the other hand, for the BA experimental group, it was observed that the structure of the mucosa was maintained in the colon tissues and such a structure was similar to that in the colon tissues of the normal group (FIG. 8).

The invention claimed is:

1. A method for treating inflammatory bowel disease of a subject in need thereof, comprising:
   administering a therapeutically effective amount of broussochalcone A to the subject.

2. The method of claim 1, wherein the inflammatory bowel disease is any one disease selected from the group consisting of Crohn's disease, ulcerative colitis, intestinal Bechet's disease, and enteritis.

3. The method of claim 1, wherein the broussochalcone A is administered in a form of a pharmaceutical composition comprising the broussochalcone A and a pharmaceutically acceptable carrier.

4. The method of claim 1, wherein the broussochalcone A is administered in a form of a foodstuff comprising the broussochalcone A and an additive.

5. The method of claim 1, wherein the broussochalcone A restores mucosa of colon of the subject.

6. The method of claim 4, wherein the foodstuff further comprises an additive selected from the group consisting of a vitamin, folate, pantothenic acid, a mineral, an amino acid, and a combination thereof.

* * * * *